(12) United States Patent
Trotta et al.

(10) Patent No.: US 11,440,975 B2
(45) Date of Patent: Sep. 13, 2022

(54) CROSS-LINKED STARCH-BASED POLYMERS FOR DRUG-DELIVERY

(71) Applicant: ROQUETTE FRERES, Lestrem (FR)

(72) Inventors: Francesco Trotta, Asti (IT); Fabrizio Caldera, Alice Castello (IT)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 17/049,185

(22) PCT Filed: Apr. 19, 2019

(86) PCT No.: PCT/EP2019/060231
§ 371 (c)(1),
(2) Date: Oct. 20, 2020

(87) PCT Pub. No.: WO2019/202148
PCT Pub. Date: Oct. 24, 2019

(65) Prior Publication Data
US 2021/0238315 A1  Aug. 5, 2021

(30) Foreign Application Priority Data
Apr. 20, 2018  (EP) .................................... 18290034

(51) Int. Cl.
C08B 37/16 (2006.01)
A61K 9/48 (2006.01)
A61K 47/40 (2006.01)

(52) U.S. Cl.
CPC ........ *C08B 37/0012* (2013.01); *A61K 9/4816* (2013.01); *A61K 47/40* (2013.01)

(58) Field of Classification Search
CPC ... A61K 9/4816; A61K 47/40; C08B 37/0012
USPC ....................................................... 424/452
See application file for complete search history.

(56) References Cited

FOREIGN PATENT DOCUMENTS

WO  2012147069 A1  11/2012
WO  2016004974 A1  1/2016

OTHER PUBLICATIONS

International Search Report and Written Opinion for Corresponding Application No. PCT/EP2019/060231 (dated Sep. 2, 2019).
Trotta et al., "Glutathione Bioresponsive Cyclodextrin Nanosponges," ChemPlusChem 81:439-443 (2015).
Jones et al., "Self-Assembly of Cross-Linked β-Cyclodextrin Nanocapsules," Chem. Commun. 11:1377-1379 (2009).

*Primary Examiner* — Ganapathy Krishnan
(74) *Attorney, Agent, or Firm* — Troutman Pepper Hamilton Sanders LLP (Rochester)

(57) ABSTRACT

The invention relates a process for preparing a cross-linked starch-based polymer comprising the following steps: 1) dissolving a starchy material in a suitable solvent to form a starchy material solution; and 2) adding a episulfide of formula (I), wherein $R_1$, $R_2$, $R_3$ and $R_4$ are independently selected from hydrogen and ($C_1$-$C_3$)alkyl in the starchy material solution in order to obtain the disulfide crosslinked starch-based polymer. In another aspect the invention concerns a disulfide-cross-linked starch-based polymer obtainable by the process of the invention, that is characterized by only disulfide bridges.

17 Claims, 10 Drawing Sheets

CROSS-LINKED STARCH-BASED POLYMERS FOR DRUG-DELIVERY

This application is a national stage application under 35 U.S.C. § 371 of PCT Application No. PCT/EP2019/060231, filed Apr. 19, 2019, which claims priority benefit of Europe Application No. 18290034.0, filed Apr. 20, 2018.

FIELD OF THE INVENTION

The present invention relates to cross-linked starch-based polymers also named as nanosponges and method for producing the same.

The cross-linked nanosponges so obtained can be used as drug delivery system.

BACKGROUND OF THE INVENTION

Starch-based nanosponges are polymers of starchy material, in particular cyclodextrins, in the form of particles, obtained by means of cross-linking with appropriate cross-linking agents.

Among starchy materials, $\alpha,\beta,\gamma$-cyclodextrins are natural or semi-synthetic cyclic oligosaccharides, being generally biodegradable; $\beta$-CD, $\gamma$-CD and certain derivatives thereof such as hydroxypropyl-$\beta$-cyclodextrin (HP-$\beta$-CD) and sulfobutyl ether-$\beta$-cyclodextrin (SBE-$\beta$-CD) are mostly used in industrial applications.

The maltodextrin used in US2010/0196542 resulted to be an alternative product for the cyclodextrins and resulted to demonstrate high yields of encapsulation, particularly of flavourings, when compared with cyclodextrins without being subjected to strict use regulations.

In WO2016/004974 it is described a cross-linked polymer obtainable by reacting a maltodextrin deriving from starch comprising amylose in the range from 25 to 50% expressed as dry weight relative to the dry weight of the starch and at least one cross-linking compound having an electropositive carbon atom selected from the group consisting of a dicarboxylic acid, dianhydrides, carbonyldiimidazole, diphenylcarbonate, triphosgene, acyl dichlorides, diisocyanates, diepoxides.

Currently known are various methods for preparing dextrin nanosponges, i.e. starch-based polymers, which envisage use of anhydrous dextrins, high temperatures, and high-boiling solvents, that are difficult to remove. In addition, said methods enable preparation of nanosponges in the form of solid blocks that then require further treatments to enable use thereof, for example washing, Soxhlet extraction and grinding.

In WO2012/147069 a method of interfacial polymerization is described, wherein the nanosponge is produced by precipitation at the interface between an organic phase and an aqueous phase that are immiscible with one another. This method advantageously enables nanoparticles to be obtained without the use of processes of a mechanical type, enables a reduction in the amount of solvents used and is generally fast.

Nanoparticles are interesting for biomedical applications, as their dimensions are close to those of biological components. In particular, different types of nanoparticles have been proposed as novel drug delivery systems for the time-controlled release of drugs targeted to specific cells or organs such that drug effects can be magnified and adverse effects reduced.

F. Trotta et al (Francesco Trotta et al. "Glutathione Bioresponsive Cyclodextrin Nanosponges", ChemPlusChem Communications, Chem PubSoc Europe) have described nanosponges as new nanosponges for the drug delivery. Specifically, in vitro and in vivo studies showed that the described nanosponges could increase the effectiveness of anti-cancer drugs encapsulated within their nanostructures. It was shown that (GSH)-responsive nanosponges dispersed in an aqueous glutathione solution had the tendency to be cleaved by reducing agents, hence these materials could be used to host and to release anticancer drugs in the presence of GSH at concentrations typical of chemoresistant cancer cells.

In this article new glutathione (GSH)-responsive materials are obtained through one-step synthesis by reacting commercially available and inexpensive 2-hydroxyethyl disulfide in the presence of $\beta$-cyclodextrin and a suitable amount of the cross-linking agent pyromellitic dianhydride. The reaction was carried out in dimethylsulphoxide (DMSO) in the presence of triethylamine.

Even if the reaction was complete in few minutes at room temperature with a yield higher than 95%, the reaction was carried out in an organic solvent, that needs to be disposed of.

Even if the results reported for these (GSH) responsive nanosponges were very promising, there is still the need of more effective (GSH)-responsive materials to be easily prepared and to be used as carrier for anticancer drugs.

SUMMARY OF THE INVENTION

The above object has been achieved by a new cross-linked polymer having disulfide bridges, that is (GSH) responsive nanosponge.

Therefore, the present invention concerns a process for preparing a glutathione (GSH) responsive cross-linked starch-based polymer comprising the following steps:
1) dissolving a starchy material in a suitable solvent to form a starchy material solution; and
2) adding a episulfide of formula (I)

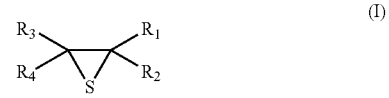

wherein $R_1$, $R_2$, $R_3$ and $R_4$ are independently selected from hydrogen and $(C_1$-$C_3)$alkyl in the starchy material solution in order to obtain the disulfide crosslinked starch-based polymer.

In the present invention when the following terms are used:
"starchy material" it is meant a material obtained from starch;
"a suitable solvent" it is meant a solvent capable to dissolve the starchy material.
Preferably the suitable solvent can be selected from organic aprotic polar solvents and water; more preferably the suitable solvent is water.
"nanosponge" it is meant a cross-linked polymer in the form of particles. In general, the average diameter of said cross-linked particles is in the range of 1 to 1000 nm. This average diameter is a hydrodynamic diameter. It can be for instance determined by the person skilled in the art by Laser Light Scattering. In general, such particles are insoluble in water at room temperature (20° C.-25° C.);

"GSH-responsive cross-linked starch-based polymer" it is meant a cross-linked starch-based polymer, which is responsive to the presence of glutathione at concentrations similar to those found in chemoresistant cancer cells;

"disulfide cross-linked starch-based polymer", it is meant a cross-linked starch-based polymer having disulfide bridges.

In another aspect the invention hence concerns a disulfide-cross-linked starch-based polymer obtainable by the process of the invention.

The present invention resulted to be extremely advantageous since the cross-linked starch-based polymer of the invention is characterized by only disulfide bonds. The cross-linked starch-based polymer of the invention is capable to encapsulate bio-substances and deliver them to the target cells. Therefore, the cross-linked starch-based polymer of the invention resulted to be a carrier, preferably a nanocarrier, for delivering drug, named here as nanosponges. Furthermore, the cross-linked starch-based polymer of the invention can be advantageously a highly cross-linked starch-based polymer having a very high content of disulfide bridges, which are actually bio-responsive in the presence of glutathione.

Therefore the invention concerns a use of the disulfide cross-linked starch-based polymer, preferably (GSH)-responsive disulfide cross-linked starch-based polymer for encapsulating and delivering drugs.

DETAILED DESCRIPTION OF THE INVENTION

Figure 1:
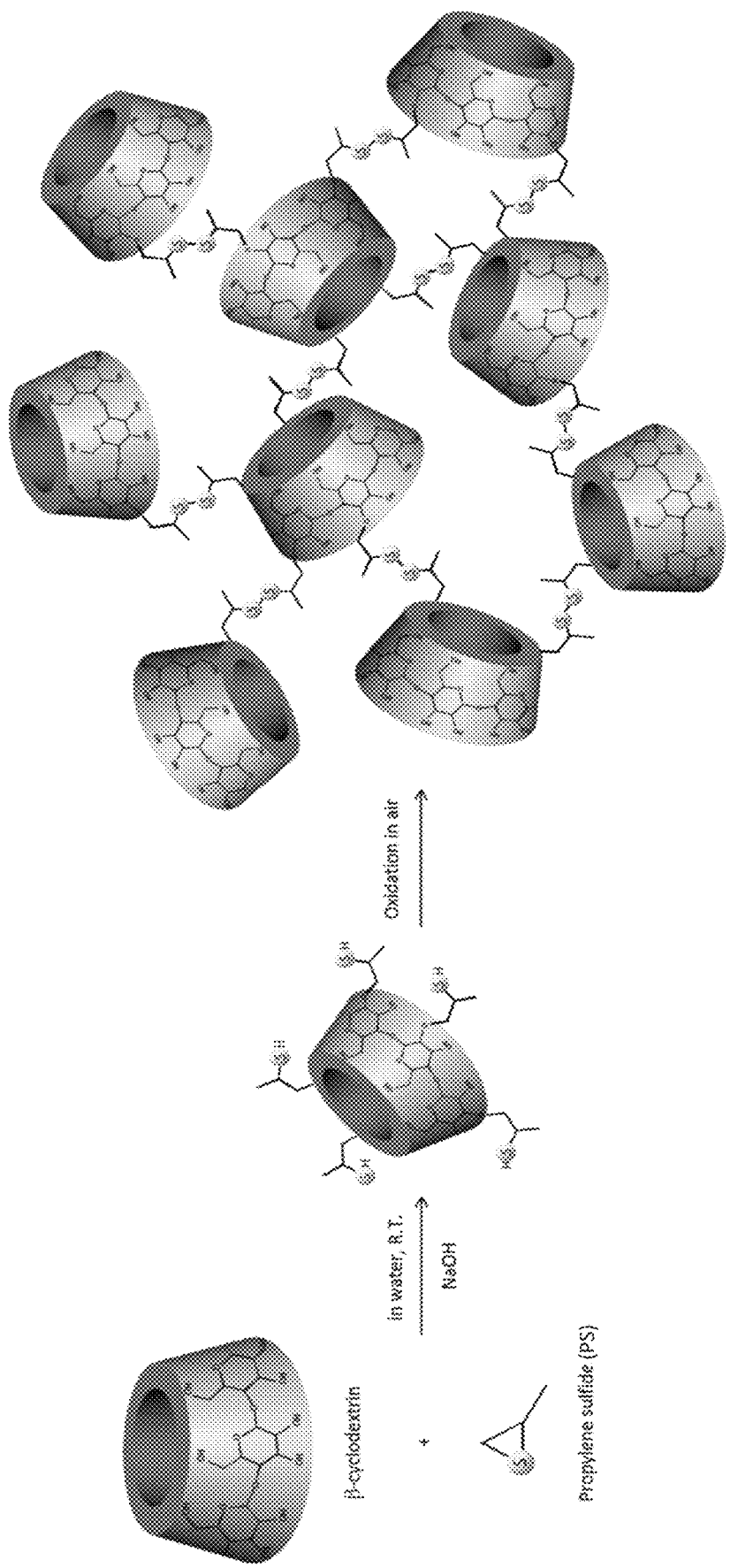
FIG. 1 is the representation of the step b) of the present invention.

The present invention hence relates to a process for preparing a cross-linked starch-based polymer comprising the following steps:

1) dissolving a starchy material in a suitable solvent to form a starchy material solution; and
2) adding a episulfide of formula (I)

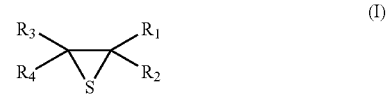

wherein $R_1$, $R_2$, $R_3$ and $R_4$ are independently selected from hydrogen and $(C_1-C_3)$alkyl in the starchy material solution in order to obtain the disulfide crosslinked In step 1) a starchy material is dissolved in a suitable solvent. Preferably the suitable solvent can be selected from organic aprotic polar solvents and water; more preferably the suitable solvent is water. Among the organic aprotic polar solvent; dimethyl sulfoxide, dimethyl formamide, dimethyl acetamide, N-methyl pyrrolidone, cyrene, dimethyl isosorbide. Preferably, cyrene and dimethyl isosorbide are preferred.

As above indicated a starchy material is a product obtained by starch.

It is reminded that the expression "starch" classically refers to the starch isolated from any suitable botanical source, by any technique well known to those skilled in the art. Isolated starch typically contains not more than 3% of impurities; said percentage being expressed in dry weight of impurities with respect to the total dry weight of isolated starch. These impurities typically comprise proteins, colloidal matters and fibrous residues. Suitable botanical source includes for instance legumes, cereals, and tubers.

Preferably, the starchy material useful to the invention is soluble in water at room temperature (20° C.-25° C.). In particular, it should be noted that starch isolated from botanical sources (native starch) is not soluble as is. It is classically in the form of cold-water insoluble granules. In order to obtain a starchy material which is cold-water soluble (soluble at room temperature), the native starch classically must undergo physical and/or chemical modification. Such modification encompasses for instance cooking, hydrolysis, for instance by way of enzymes, heat treatment, chemical treatment for instance with an acid, or combination thereof.

Preferably, the starchy material can be selected from the group consisting of a cyclodextrins, a dextrin, and a maltodextrin, and a combination thereof.

When the starchy material is a cyclodextrin, it can be α-cyclodextrin, β-cyclodextrin or γ-cyclodextrins, preferably β-cyclodextrin.

In one embodiment the starchy material is a maltodextrin. The expression "maltodextrin" classically refers to the starchy material obtained by acid and/or enzymatic hydrolysis of starch. Referring to the regulatory status, the maltodextrins have a dextrose equivalent (DE) of 1 to 20.

When the starchy material is a maltodextrin, it is preferably derived from cereal and/or legume starch, still preferably from pea starch, in particular smooth pea, or from maize starch, preferably from waxy maize starch.

In a first preferred embodiment when the starchy material is a maltodextrin, in particular derived from pea starch, the maltodextrin is derived from starch having amylose content of at least 25%, expressed as dry weight relative to the dry weight of the starch, preferably of at least 30%, still preferably of at least 35%. This amylose content is preferably selected in the range from 25 to 50% expressed as dry weight relative to the dry weight of the starch, more preferably from 30% to 40%, still more preferably from 35% and 40%, for instance from 35% and 38%.

In a second preferred embodiment, in particular when the maltodextrin is derived from maize starch, especially from waxy maize starch, the maltodextrin useful to the invention is derived from starch having amylopectin content of at least 50% expressed as dry weight relative to the dry weight of the starch, preferably of at least 60%, more preferably of at least 70%, still more preferably of at least 80%, still more preferably of at least 90%, still more preferably of at least 95%, for instance of at least 98%.

Preferably in the present invention when the starchy material is a maltodextrin, the maltodextrin has a dextrose equivalent (DE) selected within the range of 1 to 18. This DE is for instance equal to 2 or 17.

Suitable maltodextrins are commercially available, for instance those marketed under the name KLEPTOSE® Linecaps (ROQUETTE) or GLUCIDEX® (ROQUETTE).

According to the invention, the starchy material can be a dextrin. The expression "dextrin" classically refers to the starchy material obtained from heating starch under dry condition, generally in the presence of an acid.

Preferably, when the starchy material of the invention is a dextrin, it is preferably derived from maize starch. Suitable dextrins are commercially available, for instance those marketed under the name STABILYS® (ROQUETTE).

Step 2) is the addition of a episulfide of Formula (I) in the starchy material solution in order to obtain the disulfide crosslinked starch-based polymer. Preferably, the addition is carried out at room temperature. Preferably $R_1$, $R_2$, $R_3$ and $R_4$ are independently hydrogen or methyl, more preferably the episulfide is propylene sulfide.

Advantageously, step 2) can be carried out directly in the starchy material solution obtained by step a) by using water as a solvent, preferably at room temperature with no need to use organic solvents. Step 2) is preferably carried out at pH in the range from 12 to 14, preferably by using NaOH.

The molar ratio between the starchy material and the episulfide of Formula (I) is in the ratio from 1:2 to 1:20, more preferably 1:5 to 1:12, still more preferably 1:10. When the starchy material is a cyclodextrin the above ratio is preferably 1:10 and the final disulfide cross-linked starch-based polymer is obtained by precipitation.

When the starchy material is a maltodextrin, the ratio is preferably 1:10 i.e. the amount of episulfide of Formula (I), preferably propylene disulfide, is equivalent to 10 moles of sulfide for each 7 moles of condensed glucose units (Molecular weight 162.15 g/mol). The final disulfide cross-linked starch-based polymer is obtained by gelification.

When the starchy material is a dextrin, the ratio is preferably 1:10, i.e. the amount of episulfide of Formula (I), preferably propylene disulfide, is equivalent to 10 moles of sulfide for each 7 moles of condensed glucose units (Molecular weight 162.15 g/mol). The final disulfide cross-linked starch-based polymer is obtained by gelification.

Step 2) allows to precipitate/gelificate the cross-linked starch-based polymer of the invention, which is characterized by only disulfide bridges and was technically characterized as it will be clear by the below experimental part.

An exemplificative representation of step 2) and of the cross-linked starch-based polymer prepared with β-cyclodextrin as starchy material is reported in FIG. 1. After step 2) the cross-linked starch-based polymer is preferably washed with water, through centrifuge cycles, until the pH of the supernatant became neutral. Then the cross-linked starch-based polymer can be rinsed with acetone and left to dry. In case the final cross-linked starch-based polymer is obtained by gelification the gels were ground in a mortar before be washed with water.

In another aspect then the invention relates to a cross-linked starch-based polymer obtainable by the process of the invention and having only disulfide bridges.

The disulfide-cross-linked starch-based polymer of the invention is preferably insoluble in organic and aqueous solvent, such as dimethylformamide, dimethylsulfoxide, acetone, ethanol, chloroform and diethylether.

Preferably, the cross-linked polymer of the invention is a nanosponge.

The disulfide cross-linked starch-based polymer of the invention is capable to encapsulate bio-substances.

On the other hand, the disulfide polymer of the invention, being capable to encapsulate substances, can be used not only in the pharmaceutical industry, but also the cosmetic industry, the food industry, the paper and non-wovens industry, textiles, super-odoriferous products and deodorants, detergents or phytosanitary products, in drink industry and insecticidal field.

The polymer of the invention allows encapsulation/inclusion/entrapment of various organic compounds with different physicochemical characteristics and sizes, such as drugs, dyes, gases, vapors.

In a further aspect the invention hence concerns the use of the disulfide cross-linked starch-based polymer of the invention for encapsulation/inclusion/entrapment of an organic compound.

Advantageously, the disulfide cross-linked starch-based polymer can be used not only to host active principle but also to deliver them to the target cells. Therefore, the cross-linked starch-based polymer of the invention, in particular in the form of nanosponges, resulted to be a nanocarrier for delivering drugs. Furthermore, the cross-linked starch-based polymer of the invention can be a highly cross-linked polymer having a very high content of disulfide bridges, which are actually bio-responsive in the presence of glutathione.

Therefore, in a preferred embodiment the invention concerns a use of the disulfide cross-linked starch-based polymer, preferably (GSH)-responsive disulfide cross-linked starch-based polymer for encapsulating and delivering drugs.

As above explained it was shown that a (GSH)-responsive disulfide cross-linked starch-based polymer dispersed in an aqueous glutathione solution had the tendency to be cleaved by reducing agents, hence the disulfide cross-linked starch-based polymer of the invention can be used to host and to release anticancer drugs in the presence of GSH at concentrations typical of chemoresistant cancer cells.

In the most preferred embodiment, the invention relates the disulfide cross-linked starch-based polymer of the invention for use in hosting and delivering anticancer drugs in chemoresistant cancer cells.

The disulfide cross-linked starch-based polymer of the invention is used in the solid state. The final cross-linked starch-based polymer is insoluble in any solvent, hence maintains its solid state when in contact with solvent. The encapsulation of the interested substance can be easily obtained by adding the selected amount of disulfide cross-linked starch-based polymer with an excess of guest molecule dissolved in suitable solvent, after stirring overnight at room temperature the encapsulation occurs and it is recovered by simply filtration under vacuum.

The invention will be now described with reference to examples of preparation of the cross-linked starch-based polymer of the invention, its characterization and examples of encapsulation/inclusion of anticancer drugs.

EXPERIMENTAL PART

Example 1: Preparation of the Cross-Linked Starch-Based Polymer of the Invention by Reacting β-Cyclodextrin and Propylene Sulfide as Cross-Linking Agent 6.00 g of β-cyclodextrin (dried in oven at 80-120° C. for at least one night) were solubilized under continuous stirring in an alkaline solution previously prepared by adding 2.00 g of sodium hydroxide to 15 mL of water. Then, 4.14 mL of propylene sulfide were introduced. After few minutes a whitish suspension was formed. In the following days, the suspension was added to an excess of acetone and centrifuged. Then, the supernatant was replaced with fresh acetone and centrifuged again.

Centrifugation/washing cycles were repeated 5-6 times with acetone and 5-6 times using water (until the pH of the supernatant became neutral). Complete purification was accomplished by 24 hours Soxhlet extraction with acetone. Finally, the powder was freeze-dried and stored in a desiccator.

Figure 2:
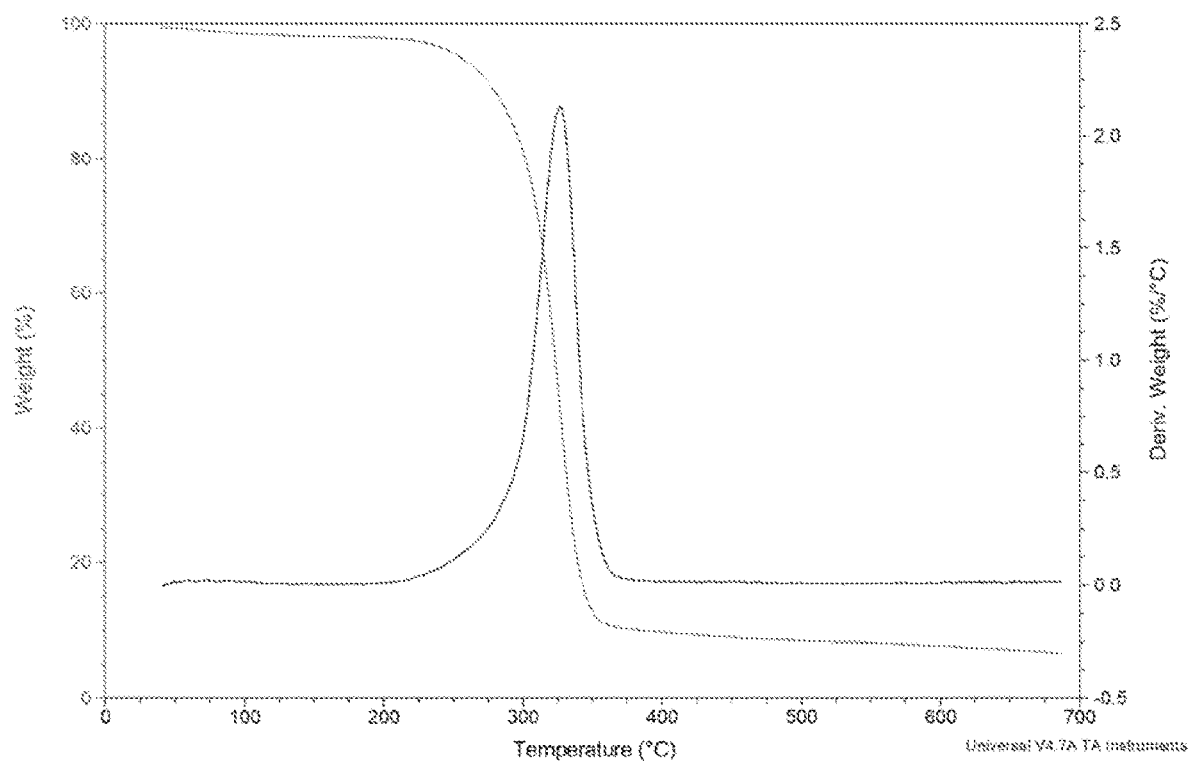
FIG. 2 shows the spectrum of TGA analysis of the cross-linked starch-based polymer of β-cyclodextrin cross-linked with propylene sulfide of example 1 TGA analysis. Method: 10° C./min to 700° C. in $N_2$.

The cross-linked starch-based polymer so obtained was analyzed by TGA analysis, using a TA Instruments TGA2050 v5.4A, with a ramp of 10° C. per minute in N2. The result of the analysis is the thermogram reported in FIG. 2. The degradation of the polymer started around 200° C. and continued up to 370° C., approximately. Nevertheless, the maximum degradation rate was reached at 325° C. At 700° C., a final residue of about 7% was registered. This thermogravimetric analysis confirmed the modification of β-cyclodextrin. The thermal degradation substantially started at a lower temperature and proceeds through a one-step pyrolysis process.

Figure 3:
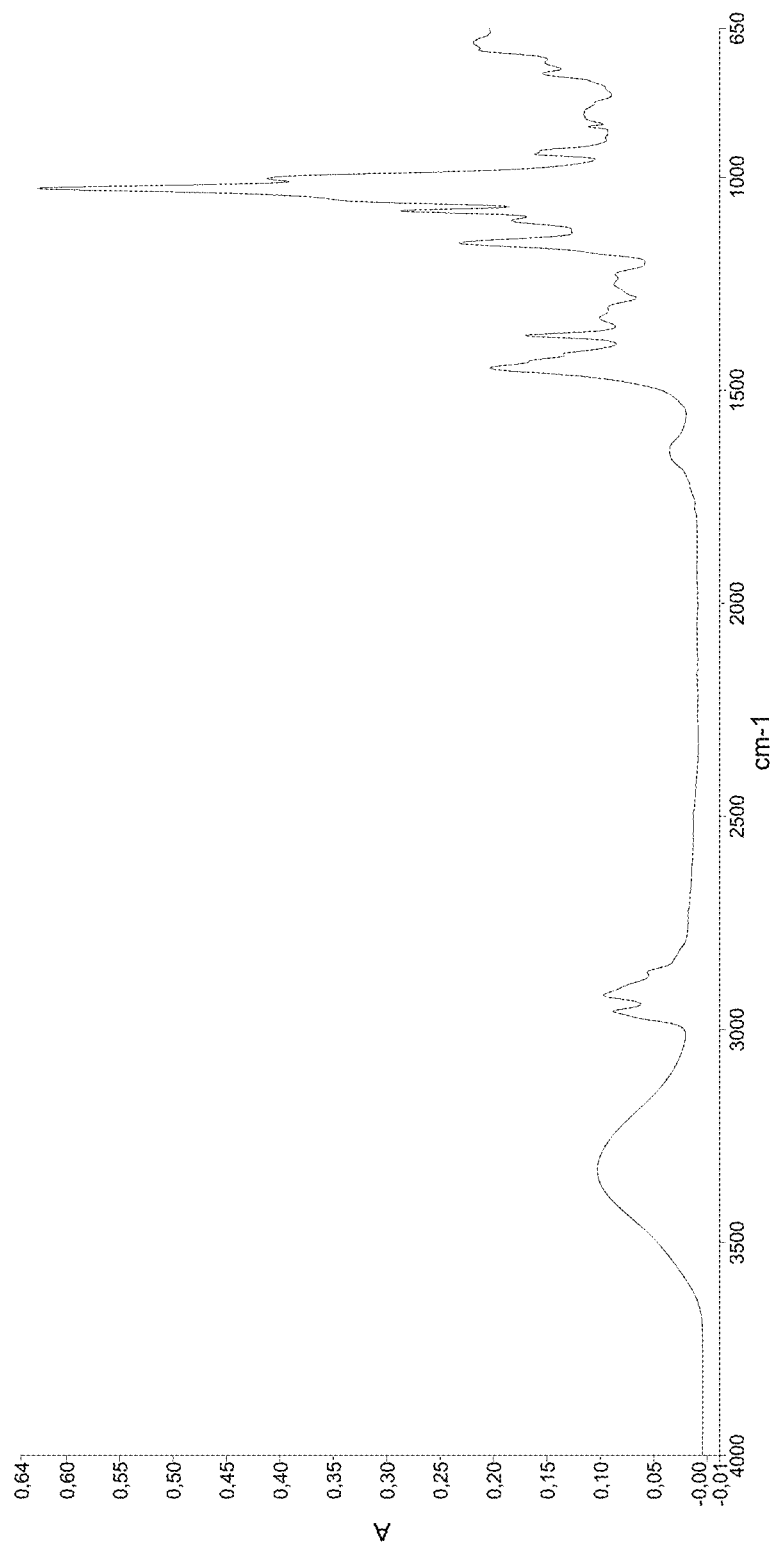
FIG. 3 shows the spectrum of FTIR-ATR analysis of the cross-linked starch-based polymer of example 1.

Furthermore, in order to better characterize the cross-linked starch-based polymer of the invention, it was analyzed with FTIR-ATR analysis, employing a PerkinElmer Spectrum 100 FT-IR spectrometer. The result of the analysis is the spectrum reported in FIG. 3. In the infrared spectrum, the peaks of the $CH_3$ groups (i.e. 2960, 1585 $cm^{-1}$), introduced by the cross-linker, can be observed in addition to the characteristic bands of the cyclodextrin units. The peaks at 2960, 1450 and 1370 cm-1, indicate a modification of the β-cyclodextrin. The most significant variation derives from the C—H stretching vibration of the $CH_3$ group introduced by propylene sulfide.

In the following table 1 the main peaks are listed, along with the corresponding absorbing groups.

TABLE 1

| Wave number ($cm^{-1}$) | Absorbing group |
|---|---|
| 3600-3100 | O—H |
| 2990-2800 | C—H |
| 1448 | C—H |
| 1371 | C—H |
| 1150-1000 | C—O |

Figure 4:
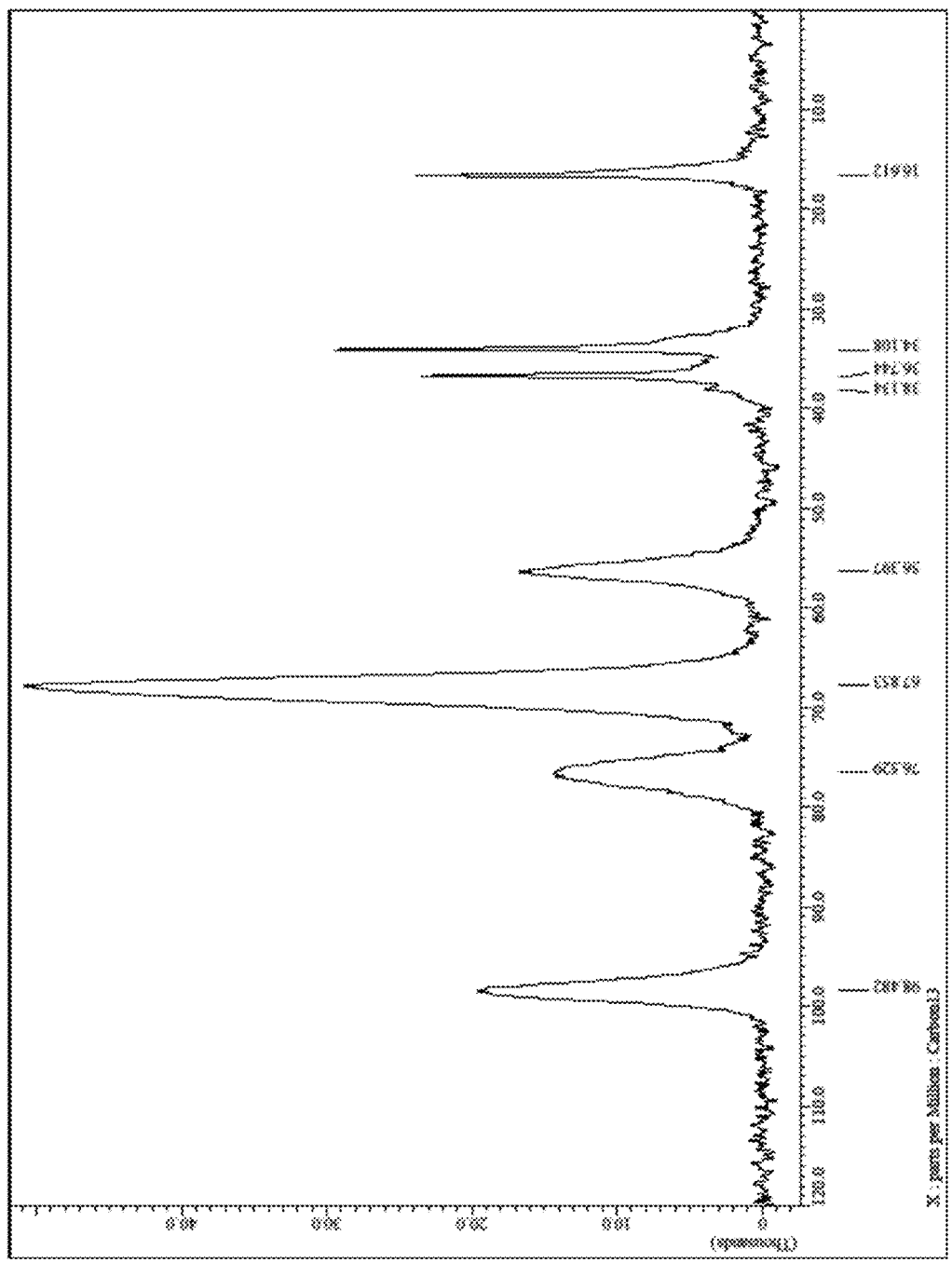
FIG. 4 shows the solid state 13C NMR spectrum of the cross-linked starch-based polymer obtained in example 1.

A further confirmation of the chemical structure of the polymer was obtained by means of solid state NMR analysis. NMR spectra were acquired with a Jeol ECZR 600 instrument, operating at 600.17 and 150.91 MHz for 1H and 13C nuclei, respectively. The solid state 13C NMR spectrum, that is reported in FIG. 4, reveals the presence of CH3 groups (16.6 ppm), derived from the polymerization reaction with propylene sulfide, thus confirming what was previously observed in the FTIR-ATR spectrum. An evidence on the crosslinked structure comes from the peaks placed in the range 36.7-38 ppm. The more intense signal (36.7 ppm) is due to CH adjacent to SH moieties, whereas the lower peak (38 ppm) can be attributed to CH groups adjacent to S—S bridges.

The polymer obtained was also characterized by means of CHNS analysis, in a Thermoscientific FlashEA 1112 Series instrument. The results are reported in the Table 2 below:

TABLE 2

| | N % | C % | H % | S % |
|---|---|---|---|---|
| Cross-linked polymer of example 1 | 0.00 | 45.54 | 7.25 | 26.43 |

The measured content of sulfur suggested a significantly higher ratio between the propylene sulfide to β-cyclodextrin the final polymer than the expected molar ratio, which was initially introduced for the synthesis reaction, i.e. a ration between propylene sulfide to β-cyclodextrin 10/1. The inventors deemed that was ascribed to a partial loss of un-reacted cyclodextrin or to a partially polymerization of episulfide.

Example 2: Preparation of the Cross-Linked Starch-Based Polymer of the Invention by Reacting α-Cyclodextrin and Propylene Sulfide as Cross-Linking Agent 3.00 g of α-cyclodextrin (dried in oven at 80-100° C. for at least one night) were solubilized under continuous stirring in an alkaline solution previously prepared by adding 1.00 g of sodium hydroxide to 7.5 mL of water. Then, 2.42 mL of propylene sulfide were introduced. After few minutes a whitish suspension was formed. In the following days, the suspension was added to an excess of acetone and centrifuged. Then, the supernatant was replaced with fresh acetone and centrifuged again.

Centrifugation/washing cycles were repeated 5-6 times with acetone and 5-6 times using water (until the pH of the supernatant became neutral). Finally, the powder was freeze-dried and stored in a desiccator.

Example 3: Preparation of the Cross-Linked Starch-Based Polymer of the Invention by Reacting γ-Cyclodextrin and Propylene Sulfide as Cross-Linking Agent 3.00 g of γ-cyclodextrin (dried in oven at 80-100° C. for at least one night) were solubilized under continuous stirring in an alkaline solution previously prepared by adding 1.00 g of sodium hydroxide to 7.5 mL of water. Then, 1.81 mL of propylene sulfide were introduced. After few minutes a whitish suspension was formed. In the following days, the suspension was added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator.

Example 4: Preparation of the Cross-Linked Starch-Based Polymer of the Invention by Reacting KLEPTOSE® Linecaps (a Maltodextrin Derived from Pea Starch, Having a DE of 17) and Propylene Sulfide as Cross-Linking Agent 3.00 g of KLEPTOSE® Linecaps (dried in oven at 80-100° C. for at least one night) were solubilized under continuous stirring in an alkaline solution previously prepared by adding 1.00 g of sodium hydroxide to 7.5 mL of water. Then, 2.07 mL of propylene sulfide were introduced. Within a few hours, a gel was formed. In the following days, the gel was broken with a spatula, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator. The disulfide cross-linked starch-based polymer was hence obtained Furthermore, in order to better characterize the cross-linked starch-based polymer of the invention, it was analyzed by means of FTIR-ATR spectroscopy.

In the following table 3 the main peaks are listed, along with the corresponding absorbing groups.

TABLE 3

| Wave number (cm$^{-1}$) | Absorbing group |
| --- | --- |
| 3600-3100 | O—H |
| 2990-2800 | C—H |
| 1448 | C—H |
| 1370 | C—H |
| 1150-1000 | C—O |

Example 5: Preparation of the Cross-Linked Starch-Based Polymer of the Invention by Reacting GLUCIDEX® 2 (a Maltodextrin Derived from Waxy Maize Starch Having a DE of 2) and Propylene Sulfide as Cross-Linking Agent 3.00 g of GLUCIDEX® 2 (dried in oven at 80-100° C. for at least one night) were solubilized under continuous stirring in an alkaline solution previously prepared by adding 1.00 g of sodium hydroxide to 15 mL of water. Then, 2.07 mL of propylene sulfide were introduced. A few minutes later, gelification occurred and a monolithic block was formed. In the following days, the gel was ground in a mortar, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator. Furthermore, in order to better characterize the cross-linked polymer of the invention, it was analyzed by means of FTIR-ATR spectroscopy.

In the following table 4 the main peaks are listed, along with the corresponding absorbing groups.

TABLE 4

| Wave number (cm$^{-1}$) | Absorbing group |
| --- | --- |
| 3600-3100 | O—H |
| 2990-2800 | C—H |
| 1448 | C—H |
| 1372 | C—H |
| 1150-1000 | C—O |

Example 6: Preparation of the Cross-Linked Starch-Based Polymer of the Invention by Reacting STABILYS® A025 (a Dextrin Derived from Maize Starch) and Propylene Sulfide as Cross-Linking Agent 3.00 g of STABILYS® A025 (dried in oven at 80-100° C. for at least one night) were solubilized under continuous stirring in an alkaline solution previously prepared by adding 1.00 g of sodium hydroxide to 15 mL of water. Then, 2.07 mL of propylene sulfide were introduced. A few minutes later, gelification occurred and a monolithic block was formed. In the following days, the gel was ground in a mortar, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator. Furthermore, in order to better characterize the cross-linked starch-based polymer of the invention, it was analyzed by means of FTIR-ATR spectroscopy.

In the following table 5 the main peaks are listed, along with the corresponding absorbing groups.

TABLE 5

| Wave number (cm$^{-1}$) | Absorbing group |
| --- | --- |
| 3600-3100 | O—H |
| 2990-2800 | C—H |
| 1448 | C—H |
| 1371 | C—H |
| 1150-1000 | C—O |

Example 7: Preparation of the Cross-Linked Starch-Based Polymer of the Invention by Reacting KLEPTOSE® Linecaps (a Maltodextrin Derived from Pea Starch, Having a DE of 17) and Ethylene Sulfide as Cross-Linking Agent 3.00 g of KLEPTOSE® Linecaps (dried in oven at 80-100° C. for at least one night) were solubilized under continuous stirring in an alkaline solution previously prepared by adding 1.00 g of sodium hydroxide to 7.5 mL of water. Then, 1.57 mL of ethylene sulfide were introduced. A few hours later, gelation occurred. In the following days, the gel was broken with a spatula, added to an excess of acetone and centrifuged.

Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator. The disulfide cross-linked starch-based polymer was hence obtained.

Example 8: Preparation of the Cross-Linked Starch-Based Polymer of the Invention by Reacting Pullulan and Propylene Sulfide as Cross-Linking Agent 3.00 g of pullulan (dried in oven at 80-100° C. for at least one night) were solubilized under continuous stirring in an alkaline solution previously prepared by adding 1.00 g of sodium hydroxide to 17 mL of water. Then, 0.83 mL of propylene sulfide were introduced. Within a few hours, a gel was formed. In the following days, the gel was broken with a spatula, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator.

Example 9: Preparation of the Cross-Linked Starch-Based Polymer of the Invention by Reacting Cyclic Nigerosyl-(1→6)-Nigerose (CNN) (a Cyclic Tetrasaccharide) and Propylene Sulfide as Cross-Linking Agent 3.00 g of CNN (dried in oven at 80-120° C. for at least one night) were solubilized under continuous stirring in an alkaline solution previously prepared by adding 0.30 g of sodium hydroxide to 5 mL of water. Then, 1.45 mL of propylene sulfide were introduced. After few minutes a whitish suspension was formed. In the following days, the suspension was added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator.

Example 10: Preparation of the Cross-Linked Starch-Based Polymer of the Invention by Reacting GLUCIDEX® 2 (a Maltodextrin Derived from Waxy Maize Starch Having a DE of 2) and Ethylene Sulfide as Cross-Linking Agent 3.00 g of GLUCIDEX® 2 (dried in oven at 80-100° C. for at least one night) were solubilized under continuous stirring in an alkaline solution previously prepared by adding 1.00 g of sodium hydroxide to 15 mL of water. Then, 1.57 mL of ethylene sulfide were introduced. Within a few hours, a gel was formed. In the following days, the gel was broken with a spatula, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator.

Example 11: Preparation of the Cross-Linked Starch-Based Polymer of the Invention by Reacting STABILYS® A025 (a Dextrin Derived from Maize Starch) and Ethylene Sulfide as Cross-Linking Agent 3.00 g of STABILYS® A025 (dried in oven at 80-100° C. for at least one night) were solubilized under continuous stirring in an alkaline solution previously prepared by adding 1.00 g of sodium hydroxide to 15 mL of water. Then, 1.57 mL of ethylene sulfide were introduced. Within a few hours, a gel was formed. In the following days, the gel was broken with a spatula, added to an excess of acetone and centrifuged. Then, the supernatant was replaced with fresh acetone and centrifuged again. Centrifugation/washing cycles were repeated 5-6 times with acetone and 5-6 times using water (until the pH of the supernatant became neutral). Finally, the powder was freeze-dried and stored in a desiccator.

Example 12: Imidacloprid Encapsulation/Absorption Test

The ability of the polymer of example 13 (γ-cyclodextrin+propylene sulfide) to absorb imidacloprid (ICP) was evaluated in comparison to a carbonate γ-cyclodextrin polymer (synthesized by reacting 6.50 g of anhydrous γ-cyclodextrin and 3.25 g of 1,1'-carbonyldiimidazole in 39 mL of anhydrous N,N-dimethylformamide at 90° C. for 4 h and subsequently cleaned with deionized water by Buchner filtration and purified by Soxhlet extraction in ethanol for 24 h). Specifically, 100 mg of polymer were added to 10 mL of a 50 ppm ICP solution, previously prepared by dissolving 5 mg of ICP in 100 mL acetonitrile-water (60/40 v/v) solution. After 72 h stirring, 1 mL of the polymer dispersion was withdrawn, filtered with a 0.2 μm syringe filter and injected in HPLC/UV. Residual unabsorbed ICP was quantified using an external calibration curve over the concentration range 10-100 ppm (HPLC method: column C18, λ detector 252 nm, mobile phase acetonitrile-water 60/40 v/v, flow 1.2 mL/min, total run time 8 min, retention time ~2.4 min).

The polymer of example 13 was able to reduce the concentration of ICP from 50 ppm to approximately 45 ppm, in other words 100 mg of polymer absorbed 50 μg of ICP (10% of the total amount of ICP). While, the amount of ICP absorbed by the carbonate polymer was lower than 1 μg.

Example 13: Clodinafop Propargyl Encapsulation/Absorption Test

The ability of the polymer of example 3 (γ-cyclodextrin+propylene sulfide) to absorb clodinafop propargyl (CFP) was evaluated in comparison to a carbonate γ-cyclodextrin polymer (synthesized by reacting 6.50 g of anhydrous γ-cyclodextrin and 3.25 g of 1,1'-carbonyldiimidazole in 39 mL of anhydrous N,N-dimethylformamide at 90° C. for 4 h and subsequently cleaned with deionized water by Buchner filtration and purified by Soxhlet extraction in ethanol for 24 h). Specifically, 100 mg of polymer were added to 10 mL of a 50 ppm CFP solution, previously prepared by dissolving 5 mg of CFP in 100 mL acetonitrile-water (60/40 v/v) solution. After 72 h stirring, 1 mL of the polymer dispersion was withdrawn, filtered with a 0.2 μm syringe filter and injected in HPLC/UV. Residual unabsorbed CFP was quantified using an external calibration curve over the concentration range 5-100 ppm (HPLC method: column C18, λ detector 230 nm, mobile phase acetonitrile-water 60/40 v/v, flow 2 mL/min, total run time 10 min, retention time ~7 min).

The polymer of example 3 was able to reduce the concentration of CFP from 50 ppm to approximately 7 ppm, in other words 100 mg of polymer absorbed 430 μg of CFP (86% of the total amount of CFP). While, the amount of CFP absorbed by the carbonate polymer was lower than 1 μg.

Example 14: Encapsulation of Doxorubicin

A) Preparation of Suspension of Blank Disulfide Cross-Linked Starch-Based Polymer Produced in Example 1

A weighted amount of disulfide cross-linked starch-based polymer produced in example 1 was suspended in a mixture of water/PEG400 (10% w/v) at the concentration of 10 mg/ml at room temperature. The suspension was then dispersed using a high shear homogenizer (Ultraturrax®, IKA, Konigswinter, Germany) for 15 minutes at 24000 rpm.

B) Preparation of Suspension of Fluorescent Disulfide Cross-Linked Starch-Based Polymer Produced in Example 1

Fluorescent labelled disulfide cross-linked starch-based polymer suspensions were obtained by adding a weighted amount of 6-coumarin (1 mg/ml) to the aqueous suspension of blank disulfide cross-linked polymer of A) (10 mg/ml, prepared as previously described) and stirring for 24 hours at room temperature in the dark. Then, the fluorescent disulfide cross-linked starch-based polymer suspension was freeze-dried using a Modulyo freeze-drier (Edwards) to obtain a powder.

C) Preparation of Doxorubicin-Loaded Disulfide Cross-Linked Starch-Based Polymer Suspension Doxorubicin-loaded disulfide cross-linked polymer were obtained by adding a weighted amount of fluorescent doxorubicin (2 mg/ml) to the aqueous suspension of disulfide cross-linked polymer (10 mg/ml). The mixture was then stirred overnight at room temperature in the dark. Subsequently, a dialysis step was performed to separate the unloaded doxorubicin.

D) Characterization of Disulfide Cross-Linked Polymer Aqueous Suspensions

The disulfide cross-linked polymer suspensions of example 14C were in vitro characterized under the physico-chemical profile.

The average diameter and polydispersity index of the disulfide cross-linked polymer suspensions were determined by photon correlation spectroscopy (PCS); the zeta potential was determined by electrophoretic mobility using a 90 Plus instrument (Brookhaven, N.Y., USA). The analyses were performed at a scattering angle of 90° and at a temperature of 25° C., using RCD S—S suspensions diluted with filtered distilled water. For the zeta potential determination, samples of diluted NS formulations were placed in the electrophoretic cell, where an electric field of approximately 15 V/cm was applied.

The physico-chemical characteristics of disulfide cross-linked polymer were also evaluated in the absence and in the presence of glutathione (50 mM).

Table 6. Physico-chemical characteristics of disulfide cross-linked polymer in the absence and in the presence of glutathione

|  | pH | Average diameter (nm) ± SD | PDI | Zeta potential (mV) ± SD |
|---|---|---|---|---|
| NO GSH | 6.46 | 1255.8 ± 66.9 | 0.302 | −14.52 ± 2.46 |
| WITH GSH (50 mM) | 3.11 | 4339.2 ± 638.2 | 0.381 | 7.54 ± 1.20 |

Figure 5:
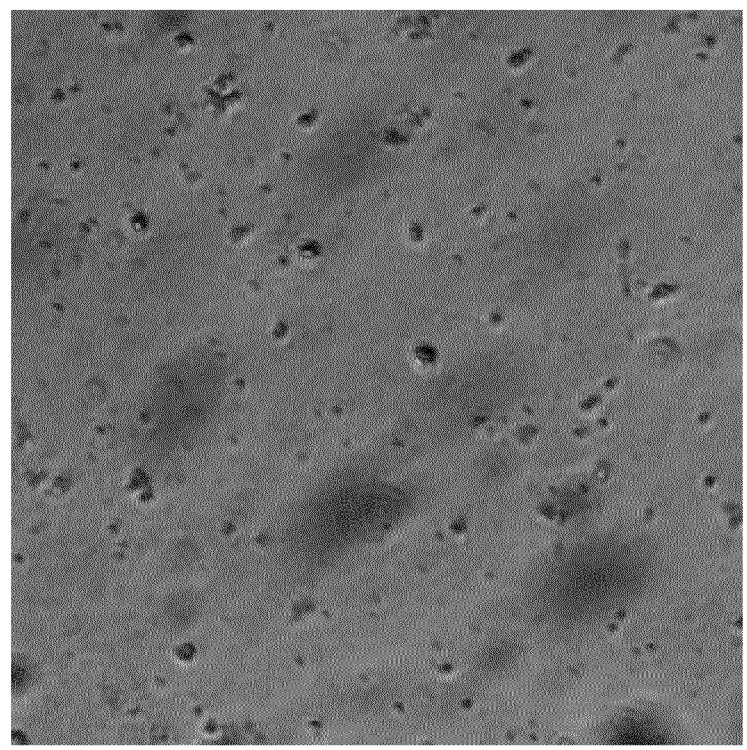
FIG. 5 is the Optical image of βCD S—S in the absence of glutathione (Magnification 630×)
Figure 6:
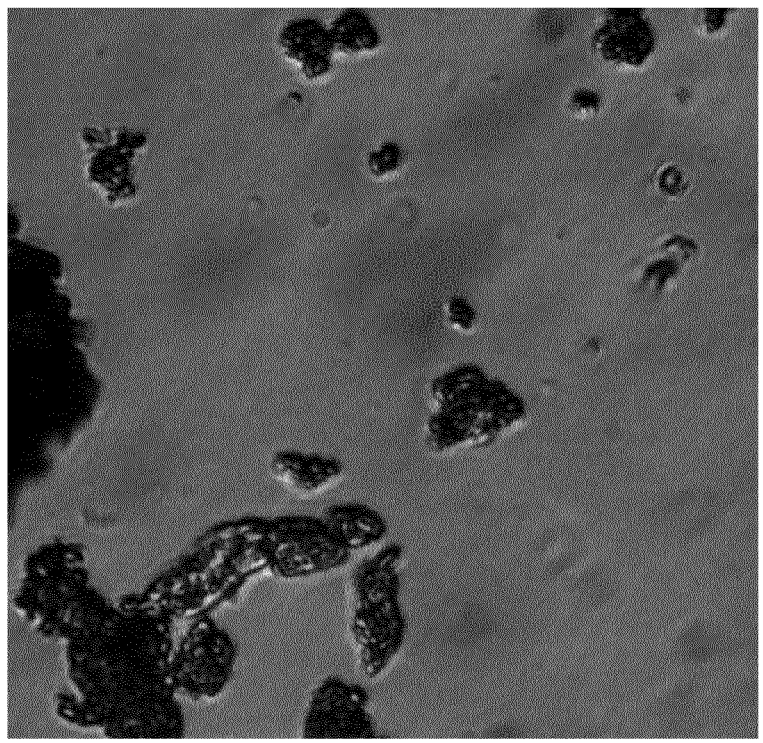
FIG. 6 is the Optical image of βCD S—S in the presence of 50 mM glutathione (Magnification 630×)

In FIG. 5 it is reported the optical image of disulfide cross-linked polymer in the absence of glutathione (Magnification 630×) and in FIG. 6 the optical image of disulfide cross-linked polymer in the presence of 50 mM glutathione (Magnification 630×). The addition of glutathione led to an increase of particle size, as revealed by both scattering light and optical microscopy analysis. The inventors ascribe this effect to the pH variation, caused by the addition of GSH, and the resulting decrease of Z potential absolute value, which favors particle aggregation.

Example 15: In Vitro Release of the Disulfide Cross-Linked Starch-Based Polymer Loaded with Doxorubicin In vitro drug release experiments were conducted in a multi-compartment rotating cell comprising a donor chamber separated by a cellulose membrane (Spectrapore, cut-off=12000 Da) from a receiving chamber. One ml of doxorubicin-loaded disulfide cross-polymer of example 14C was placed in the donor chamber. The receiving compartment contained 1 ml of phosphate buffered saline (PBS) at pH 7.4. In vitro release studies were carried out in the presence of glutathione (50 mM) in the receiving compartment. The receiving phase was withdrawn at regular intervals and completely replaced with the same amount of fresh solution, to maintain sink conditions. The concentration of doxorubicin in the withdrawn samples was detected by HPLC.

HPLC Quantitative Determination of Doxorubicin

Quantitative determination of doxorubicin was carried out by an HPLC system consisting of a pump (Shimadzu LC-9A PUMP C) equipped with fluorescence detector (Chrompack). Analyses were performed using an Agilent TC C18 column (250 mm×4.6 mm, 5 μm). The mobile phase was a mixture of KH2PO4 0.01 M (pH 1.4), acetonitrile and methanol (65:25:10 v/v/v), degassed and pumped through the column with a flow rate of 1 ml/min. The column effluent was monitored at excitation and emission wavelengths of 480 and 560 nm, respectively. The external standard method was used to calculate the drug concentration. For this purpose, 1 mg of doxorubicin was weighed, placed in a volumetric flask, and dissolved in water to obtain a stock standard solution. This solution was then diluted using the mobile phase, providing a series of calibration solutions, subsequently injected into the HPLC system. Linear calibration curve was obtained over the concentration range of 5-100 ng/mL with a regression coefficient of 0.999.

The in vitro release kinetics of doxorubicin from disulfide cross-linked polymer of example 14C in the absence or in the presence of glutathione (50 mM) in the receiving phase are reported in the table 7 below and represented in FIG. 7.

| Time (h) | NO GSH % doxorubicin released | GSH (50 mM) % doxorubicin released |
|---|---|---|
| 0 | 0.00 | 0.00 |
| 0.25 | 0.43 | 5.06 |
| 0.5 | 0.87 | 10.04 |
| 0.75 | 1.20 | 15.08 |
| 1 | 1.84 | 20.17 |
| 1.5 | 2.65 | 26.74 |
| 2 | 3.44 | 35.27 |
| 3 | 5.28 | 47.77 |
| 4 | 6.60 | 60.43 |
| 5 | 7.88 | 73.05 |
| 6 | 9.96 | 84.86 |

The disulfide cross-linked polymer of example 14 (named as RCD NS S—S) was hence evaluated for delivering doxorubicin in in the presence or in absence of 50 nM of glutathione.

Figure 7:
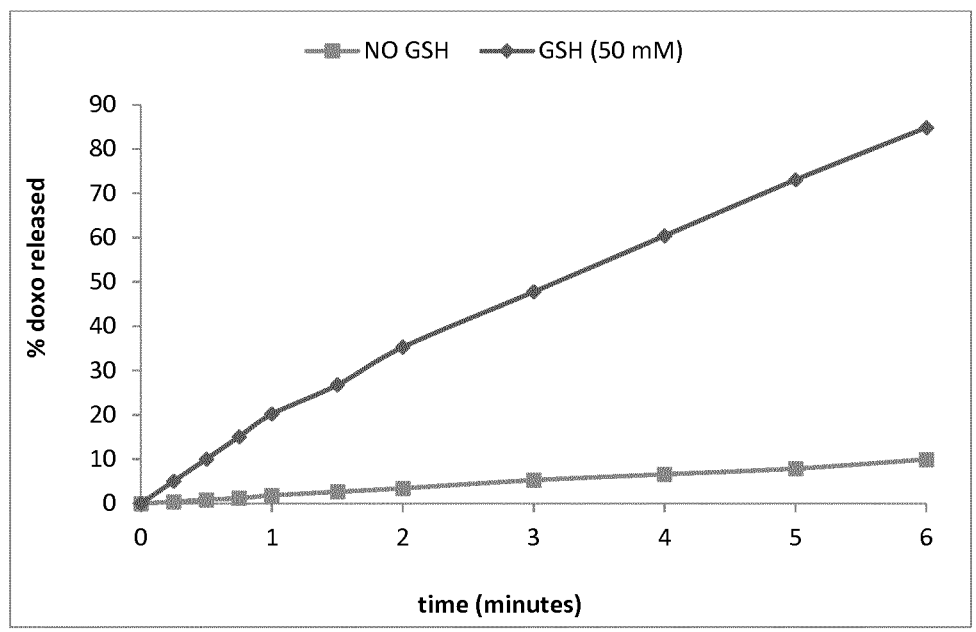
FIG. 7 shows the release kinetics of doxorubicin as indicated in the example 15.

As it can be seen from FIG. 7 doxorubicin was released by the disulfide cross-linked polymer in a linear way, thus demonstrating that the cross-linked starch-based polymer of the invention was a doxorubicin delivery system in the presence of glutathione.

This example demonstrated also that the disulfide cross-linked polymer of the invention was a delivery drug system capable to release antitumoral agents encapsulated in the cross-linked starch-based polymer itself when glutathione is present as in the concentration as in the cancer cells.

Example 16

Figure 8:
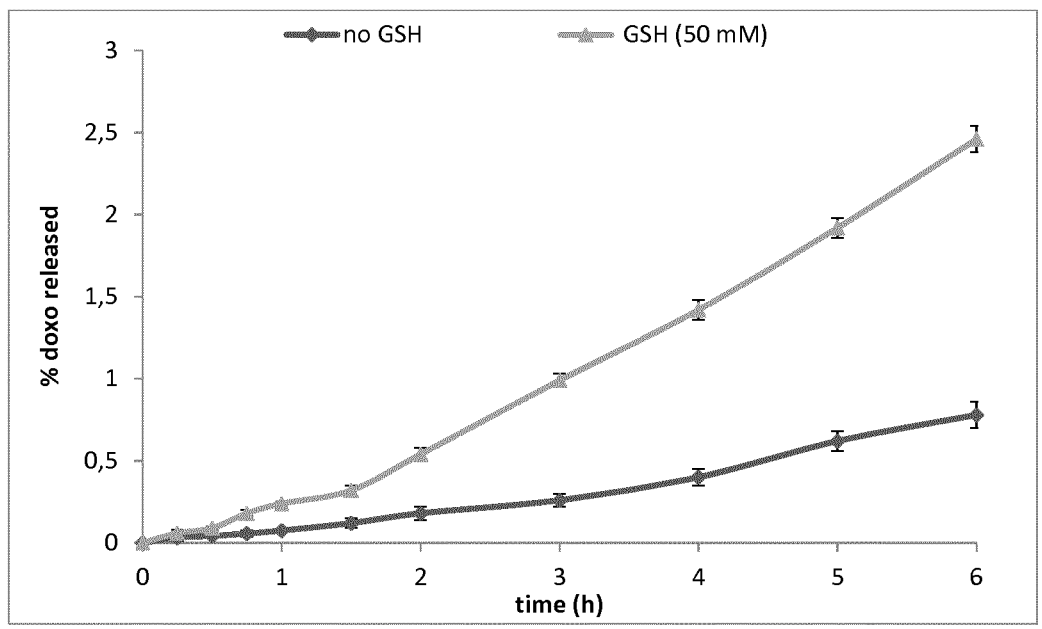
FIG. 8 shows the release of doxorubicin from doxorubicin-loaded 2HES-NS in the absence or presence of glutathione of example 16.

For comparison purposes, a nanosponge containing disulfide bridges (sulphur content 0.62 wt %), deriving from 2-hydroxyethyl disulfide (2HES), was synthesized by reacting β-cyclodextrin and 2HES with pyromellitic dianhydride, following the procedure reported in Trotta et al., ChemPlusChem 2016, 81, 439-443. Specifically, 1.00 g of anhydrous n-CD and 0.10 g of 2HES were solubilized in 4.0 mL of dimethyl sulfoxide. Afterwards, 1 mL of triethylamine and 2.75 g of pyromellitic dianhydride were introduced in the solution and stirred until a rigid gel was formed. 24 h later, the gel was ground in a mortar, washed through Buchner filtration with deionized water, and then acetone, and finally purified by Soxhlet extraction with acetone for 14 hours. 2HES-nanosponge was loaded with doxorubicin, following the procedure reported in example 14 C. Then, the in vitro release study of doxorubicin from 2HES-nanosponge was performed in the absence and in the presence of glutathione, as reported in example 15. As is clear from FIG. 8, glutathione triggered a threefold faster release of doxorubicin, whose content in the receiving phase increased from 0.8% to 2.5% in the presence of 50 mM glutathione.

Figure 9:
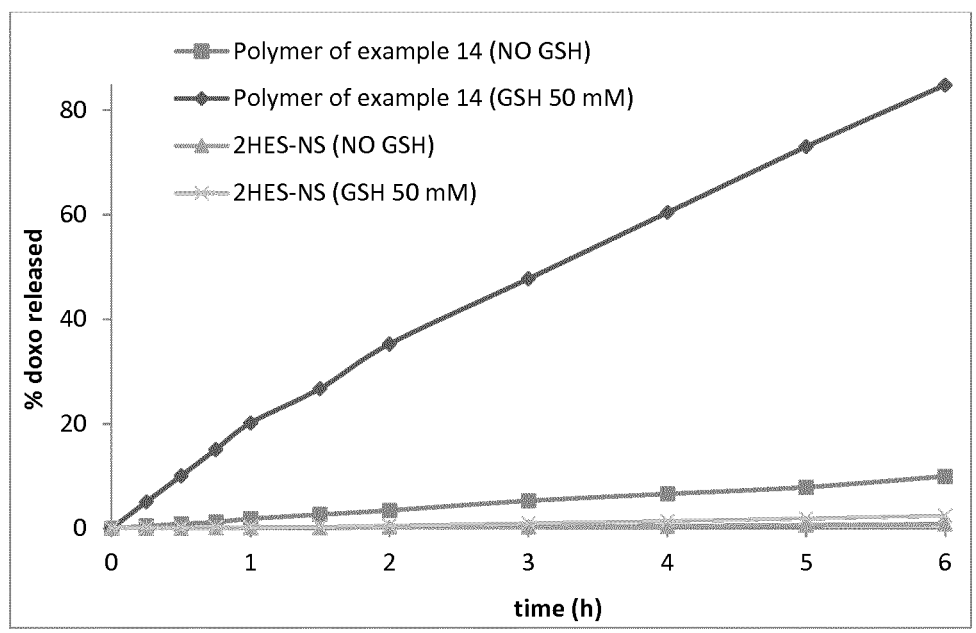
FIG. 9 shows the comparison of release kinetics of example 16.
Figure 10:
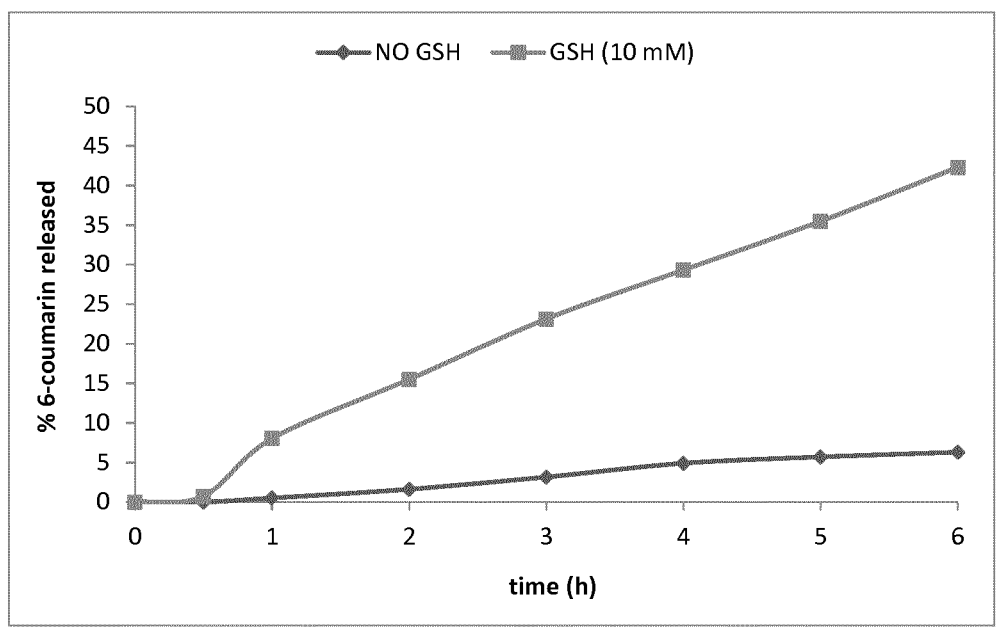
FIG. 10 shows the release kinetics of coumarin as indicated in the example 17.

However, compared to 2HES-nanosponge, the polymer of example 14 C exhibited a significantly higher sensitivity to glutathione, since the amount of doxorubicin, released after 6 h, increased from approximately 10% to 85% (eightfold increase), when glutathione was introduced at a 50 mM concentration (FIG. 9).

Example 17

In vitro drug release of 6-coumarin from fluorescent labelled fluorescent disulfide cross-linked polymer of example 14 B) was evaluated in a multi-compartment rotating cell comprising a donor chamber separated by a cellulose membrane (Spectrapore, cut-off=12000 Da) from a receiving chamber. One ml of fluorescent labelled βCD S—S was placed in the donor chamber. The receiving compartment contained 1 ml of a mixture of water/Tween20 (0.5% w/v). The in vitro release study was also carried out in the presence of glutathione (10 mM) in the receiving compartment. The receiving phase was withdrawn at regular intervals and completely replaced with the same amount of fresh solution, to maintain sink conditions.

The concentration of 6-coumarin in the withdrawn samples was determined using a fluorimeter detector (Ex 450 nm, Em 480 nm).

The results of the in vitro release kinetics of 6-coumarin from fluorescent labelled cross-linked starch-based polymer in the absence or in the presence of glutathione (10 mM) in the receiving phase are reported in Table 8 and represented in FIG. 9.

TABLE 8

| time (h) | NO GSH<br>% 6-coumarin released | GSH (10 mM)<br>% 6-coumarin released |
|---|---|---|
| 0 | 0.00 | 0.00 |
| 0.5 | 0.01 | 0.74 |
| 1 | 0.52 | 8.05 |
| 2 | 1.63 | 15.51 |
| 3 | 3.17 | 23.15 |
| 4 | 4.91 | 29.32 |
| 5 | 5.71 | 35.48 |
| 6 | 6.31 | 42.31 |

In fact, the new polymers of the invention were responsive to the presence of GSH (disrupting S—S bonds) and faster release of coumarin used as a fluorescent probe. In the absence of GSH only negligible release was observed.

The invention claimed is:

1. A process for preparing a disulfide cross-linked starch-based polymer comprising the following steps:
   1) dissolving a starchy material in a suitable solvent to form a starchy material solution; and
   2) adding an episulfide of formula (I)

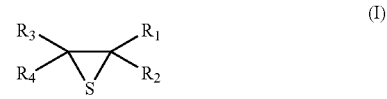

wherein $R_1$, $R_2$, $R_3$ and $R_4$ are independently selected from hydrogen and $(C_1$-$C_3)$alkyl in the starchy material solution in order to obtain the disulfide crosslinked starch-based polymer, and wherein the starchy material is selected from the group consisting of a cyclodextrin, a dextrin, a maltodextrin, and a combination thereof.

2. The process according to claim 1, wherein the starchy material is a cyclodextrin selected from α-cyclodextrin, β-cyclodextrin, and γ-cyclodextrin.

3. The process according to claim 1, wherein the starchy material is a maltodextrin derived from cereal starch, legume starch, or waxy maize starch.

4. The process according to claim 1, wherein the starchy material is a maltodextrin derived from pea starch.

5. The process according to claim 4, wherein the maltodextrin derived from pea starch has an amylose content in the range from 25% to 50% dry weight relative to the dry weight of starch.

6. The process according to claim 1, wherein in step 1) the solvent is selected from organic aprotic polar solvents and water.

7. The process according to claim 1, wherein step 2) is carried out at room temperature.

8. The process according to claim 1, wherein step 2) is carried out at pH in the range from 12 to 14.

9. The process according to claim 8, wherein the molar ratio between starchy material and the episulfide is in the ratio from 1:2 to 1:20.

10. The process according to claim 9, wherein when the starchy material is a cyclodextrin, the ratio is 1:10, and the final disulfide cross-linked starch-based polymer is obtained by precipitation.

11. The process according to claim 9, wherein the starchy material is a maltodextrin or a dextrin, and the ratio is 1:10.

12. The process according to claim 1, wherein in the episulfide of formula (I), $R_1$, $R_2$, $R_3$ and $R_4$ are independently selected from H and $CH_3$.

13. The process according to claim 12, wherein the episulfide of formula (I) is propylene disulfide.

14. A disulfide cross-linked starch-based polymer obtainable by the process of claim 1.

15. A method for encapsulation/inclusion/entrapment of an organic compound, wherein the method comprises the step of adding the disulfide cross-linked starch-based polymer of claim 14 with an excess of the organic compound dissolved in a solvent thus obtaining the organic compound encapsulated, included, or entrapped in the disulfide cross-linked starch-based polymer.

16. A method for encapsulating and delivering a drug, wherein said method comprises the steps of:
adding using the disulfide cross-linked starch-based polymer according to claim 14 with an excess of the drug dissolved in a solvent thus obtaining the drug encapsulated in the disulfide cross-linked starch-based polymer; and
delivering the encapsulated drug.

17. A method for hosting and delivering an anticancer drug in chemoresistant cancer cells, wherein said method comprises the steps of:
adding the disulfide cross-linked starch-based polymer according to claim 14 with an excess of the anticancer drug dissolved in a solvent thus obtaining the anticancer drug hosted in the disulfide cross-linked starch-based polymer; and
delivering the hosted anticancer drug in chemoresistant cancer cells.

\* \* \* \* \*

UNITED STATES PATENT AND TRADEMARK OFFICE
CERTIFICATE OF CORRECTION

PATENT NO. : 11,440,975 B2
APPLICATION NO. : 17/049185
DATED : September 13, 2022
INVENTOR(S) : Trotta et al.

It is certified that error appears in the above-identified patent and that said Letters Patent is hereby corrected as shown below:

In the Claims

At Claim 16, Column 17, Line 17, the word "using" after the word "adding" should be deleted.

Signed and Sealed this
Twentieth Day of December, 2022

Katherine Kelly Vidal
*Director of the United States Patent and Trademark Office*